United States Patent [19]
Kroll et al.

[11] Patent Number: 5,662,696
[45] Date of Patent: Sep. 2, 1997

[54] ONE PIECE DISPOSABLE THRESHOLD TEST CAN ELECTRODE FOR USE WITH AN IMPLANTABLE CARDIOVERTER DEFIBRILLATOR SYSTEM

[76] Inventors: Mark W. Kroll, 13011 Brenwood Trail, Minnetonka, Minn. 55343; Roger W. Dahl, 112 150th La. NW., Andover, Minn. 55304; Stephen K. Sundquist, 18027 Turnberry Cir., Minnetonka, Minn. 55345; Randall S. Nelson, 7419 Pinehurst Ct., Pine Springs, Minn. 55115

[21] Appl. No.: 535,666

[22] Filed: Sep. 28, 1995

[51] Int. Cl.⁶ .................... A61N 1/375; A61N 1/39
[52] U.S. Cl. .................... 607/116; 607/36; 607/37; 607/8
[58] Field of Search .................... 607/1, 2, 4, 5, 607/8, 10, 27, 28, 36, 37, 116, 115, 119

[56] References Cited

U.S. PATENT DOCUMENTS

| | | |
|---|---|---|
| 3,747,605 | 7/1973 | Cook .................... 607/8 |
| 5,383,914 | 1/1995 | O'Phelan . |
| 5,405,363 | 4/1995 | Kroll et al. .................... 607/5 |
| 5,411,539 | 5/1995 | Neisz .................... 607/36 |

FOREIGN PATENT DOCUMENTS 0473002  3/1992  European Pat. Off. .................... 607/8

*Primary Examiner*—William E. Kamm
*Assistant Examiner*—Kennedy J. Schaetzle
*Attorney, Agent, or Firm*—Brad Pedersen

[57] ABSTRACT

The present invention is a one piece, disposable pulse generator emulator for emulating a subcutaneous implantable cardioverter defibrillator (ICD) having an active housing electrode. The emulator of the present invention is for use with an external test system to screen a patient for candidacy for an ICD by determining the patient's minimum defibrillation threshold voltage. The one piece, disposable emulator has a housing that has substantially the same conductive geometry as the desired implantable pulse generator.

21 Claims, 3 Drawing Sheets

ONE PIECE DISPOSABLE THRESHOLD TEST CAN ELECTRODE FOR USE WITH AN IMPLANTABLE CARDIOVERTER DEFIBRILLATOR SYSTEM

TECHNICAL FIELD

The present invention relates generally to the field of automatic, implantable cardioverters and defibrillators. In particular, the present invention relates to a test can electrode for screening a patient for candidacy for an implantable cardioverter defibrillator.

BACKGROUND OF THE INVENTION

Under existing medical practice, each time an implantable cardioverter defibrillator (ICD) is implanted in a human patient, an intraoperative testing procedure is attempted in order to determine a minimum defibrillation threshold (DFT) in terms of the number of joules of electrical energy required to successfully defibrillate a patient for the particular electrode lead combination which has been implanted in that patient. The intraoperative testing procedure involves inducing ventricular fibrillation in the heart and then immediately delivering a defibrillation countershock through the implanted electrode leads of a specified initial threshold energy, for example, 20 joules for a monophasic countershock. If defibrillation is successful, a recovery period is provided for the patient and the procedure is usually repeated a small number of times using successively lower threshold energies until the defibrillation countershock is not successful or the threshold energy is lower than about 10 joules. If defibrillation is not successful subsequent countershocks of 35 joules or more are immediately delivered to resuscitate the patient. After a recovery period, the procedure is repeated using a higher initial threshold energy, for example, 25 joules. It is also possible that during the recovery period prior to attempting a higher initial threshold energy, the electrophysiologist may attempt to lower the DFT for that patient by moving or changing the electrode leads.

The intraoperative testing procedure is designed to accomplish a number of objectives, including patient screening and establishing a minimum DFT for that patient. Typically, if more than 30 to 35 Joules are required for successful defibrillation with a monophasic countershock the patient is not considered to be a good candidate for an ICD and alternative treatments are used. Otherwise the lowest energy countershock that results in successful defibrillation is considered to be the DFT for that patient. The use of the lowest energy possible for a defibrillation countershock is premised on the accepted guideline that a countershock which can defibrillate at a lower energy decreases the likelihood of damaged to the myocardial tissue of the heart.

Recent efforts to improve the efficiency of ICD's have led manufacturer's to produce ICD's which are small enough to be implanted in the pectoral region, thereby enabling the housing of the ICD to form a subcutaneous electrode, such as described in U.S. Pat. No. 5,405,363. Further developments in the industry have led to active housing electrode emulators as disclosed in U.S. Pat. No. 5,411,539 to Neisz in order to simulate an active housing electrode during the testing procedure. The system described by Neisz in the '539 patent provides a largely reusable active housing electrode emulator for screening patients for suitability for permanent implantation with an ICD having an active housing electrode. The system disclosed in the '539 patent has a reusable, sterilizable conductive can conforming to the dimensions of the ICD desired to be implanted. The reusable emulator has an electrical and mechanical attachment mechanism to connect to a standard ICD lead. Once DFT testing is completed, the ICD lead is then disposed of.

As described in the Neisz '539 patent, the rational for using reusable emulation housing electrodes is that they will save money by not having to dispose of the emulation housing electrodes after the testing of a patient is completed. In actuality, the use of reusable housing electrodes may cost more in the long run because such emulation housing electrodes must be constructed of high quality, expensive materials, for example platinum or MP35N. Over time, the housing electrode will begin to anodize which causes the impedance to change, which in turn changes the electrical characteristics of the electrode. This anodization may have a profound effect on the test results and therefore, the emulator must be disposed of when anodization occurs.

Additionally, the Neisz '539 patent teaches of using a standard ICD lead and then disposing of such lead when DFT testing is complete. Specifically, column 7, lines 50-51, state that "After testing is complete, the lead component 90 may be disposed of . . . ". Such leads are very expensive because they are designed to be implanted into patient's body. The leads must be made of governmentally approved materials that are biocompatible and durable enough to last in contact with body fluids for many years. Also, the leads contain a header that includes a pair of female receptacles and expensive through hole connections for connecting the female receptacles of the header to conductive wires in the lead.

While the existing techniques for performing intraoperative testing using an active housing electrode emulator to establish a minimum DFT for a patient are acceptable, it would be advantageous to provide an active housing electrode emulator which improves performance at a reduced per use cost.

SUMMARY OF THE INVENTION

The present invention is a one piece, disposable pulse generator emulator for emulating a subcutaneous implantable cardioverter defibrillator (ICD) having an active housing electrode. The emulator of the present invention is for use with an external test system to screen a patient for candidacy for an ICD by determining the patient's minimum defibrillation threshold voltage. The one piece, disposable emulator has a housing that has substantially the same conductive geometry as does the desired implantable pulse generator.

A conductive lead having a proximal and distal end is provided with the proximal end being permanently attached to the housing. Because the lead is connected directly to the housing, there is no need for a header as in the prior art which saves money by eliminating expensive feedthroughs and a connector block. Additionally, the leads of the present invention are specially designed, inexpensive leads, designed for use with only one patient. The leads of the present invention, need not be constructed of exotic alloys such as MP35N or platinum iridium with insulation manufactured with special grades of polyurethane or silicon like required in standard ICD leads. A test system connection pin is also provided at the distal end of the lead for connection to an external test system.

DETAILED DESCRIPTION OF THE PREFERRED EMBODIMENT

Prior to giving a detailed description of the present invention, a brief description of the common physical arrangement of an implantable cardioverter defibrillator (ICD) adopted for implantation in the pectoral region will be presented to provide a context for the remainder of the description.

Figure 1:
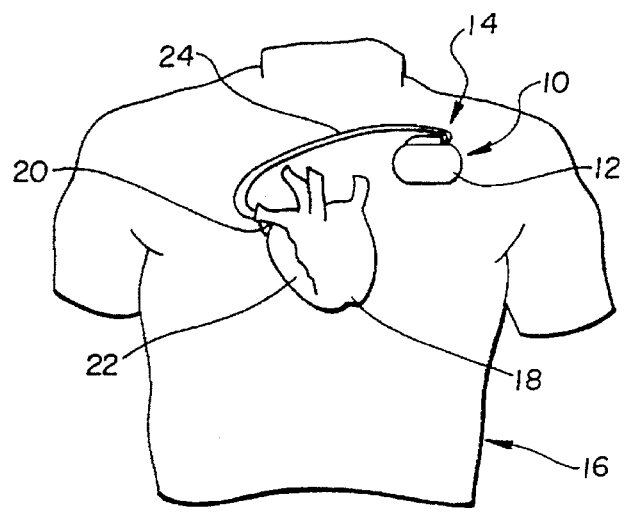
FIG. 1 is a frontal plan view illustrating an automatic implantable cardioverter defibrillator having an active housing electrode, implanted in the pectoral region of a human patient.

FIG. 1 illustrates an ICD 10 have a housing 12 that forms a subcutaneous electrode. ICD 10 is shown implanted in the pectoral region 14 of a patient 16, substantially adjacent to the patient's heart which is illustrated schematically at 18. The heart includes, among other things, a superior vena cava 20 and a right ventricle 22, which are the most relevant portions of the heart for the present discussion. A conductive lead 24 is provided for carrying a plurality of electrodes, the lead having first and second ends 25, 27. First end 25 is connected to pulse generator 12 and second end 27 passes through superior vena cava 20 and into right ventricle 22. For a more detailed discussion of ICD 10, reference is made to U.S. Pat. No. 5,405,363, the disclosure of which is incorporated hereby reference.

Figure 2:
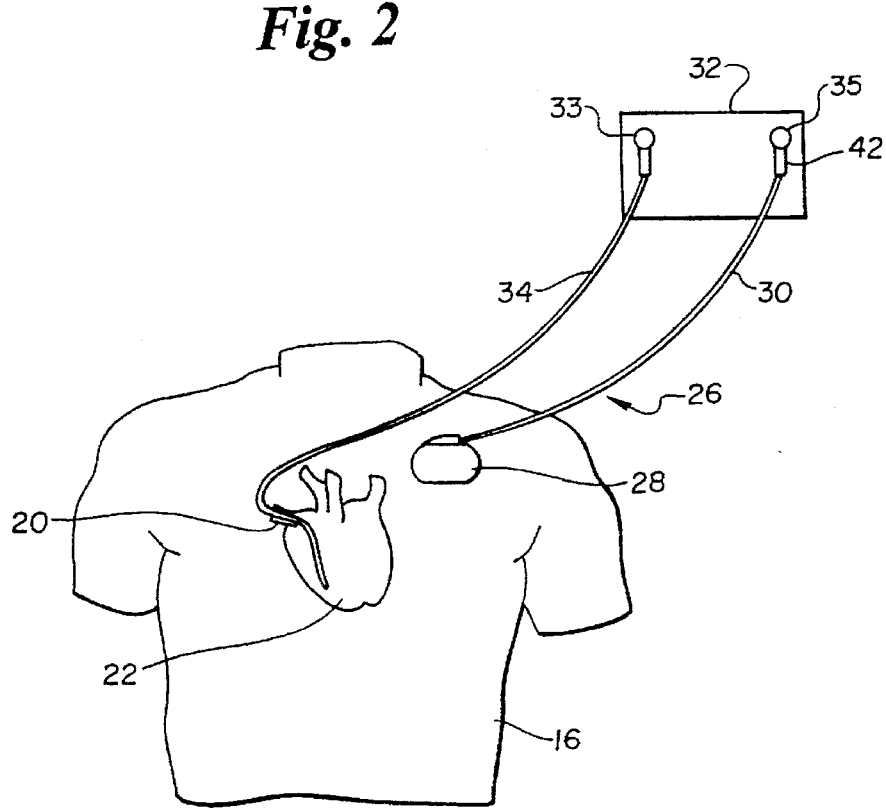
FIG. 2 is a frontal plan view illustrating the one piece disposable pulse generator emulator of the present invention implanted in the pectoral region of a human patient connected to an external test system.

FIG. 2 illustrates a one piece disposable pulse generator emulator 26 made according to the present invention that includes an active housing electrode emulation portion 28 and a conductive lead 30 which is fixedly attached to emulator housing 28. As was illustrated in FIG. 1, in a normal active housing electrode ICD configuration, conductive lead 24 will be connected to the ICD and inserted into the right ventricle of the heart. In the emulation system of the present invention, an external test system 32 is provided which has all the capabilities of an implanted defibrillator and which can emulate all of the functions of an implanted system without contaminating an ICD. Examples of known external test systems include the Ventak™ ECD by CPI, the External Tachyrhythmia Control Device (ETCD™) by Medtronic, Inc., and the Ventrix High Voltage Stimulator (HVS-02™) by Ventrix, Inc.

Test system 32 has first and second connection portions 33, 35 for connecting to a plurality of leads. A standard ICD electrode lead 34 is connected to first connection port 33 and is inserted into the patient's right ventricle via superior vena cava 20. Conductive lead 30 is connected to the second port 35 and is fixedly attached to emulator housing 28 as stated above. External system 32 allows the physician to determine a minimum defibrillation threshold (DFT) energy required for the patient. The testing procedure involves inducing ventricular fibrillation in the heart and then immediately delivering a defibrillation countershock through electrodes connected to leads 30, 34 of a specified initial threshold energy, for example, 20 joules for a monophasic countershock. If defibrillation is successful, a recovery period is provided by the patient and the procedure is usually repeated a small number of times using successively lower threshold energies until the defibrillation countershock is not successful or the threshold energy is lower than about 10 joules. If defibrillation is not successful, subsequent countershocks of 35 joules or more are immediately delivered to resuscitate the patient. After a recovery period, the procedure is repeated using a higher initial threshold energy, for example, 25 joules.

Figure 3:
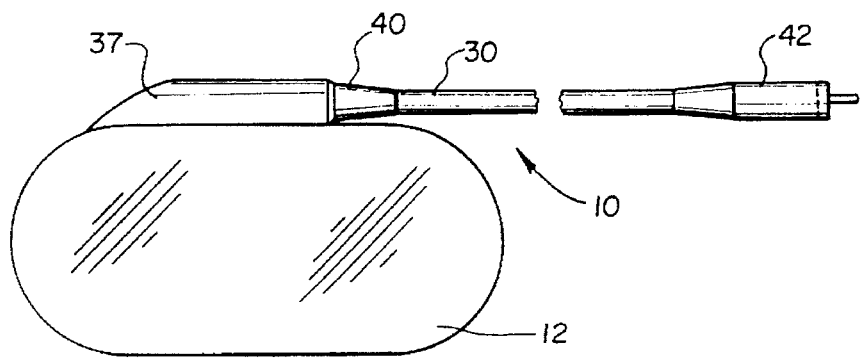
FIG. 3 is a front plan view of the one piece disposable emulator unit of the present invention.

FIG. 3 is an enlarged front plan view of the one piece disposable emulator 10 of the present invention. The emulator housing 28 is chosen to replicate the approximate length and height of the desired implanted ICD. It is important to note that while it is ideal if the emulator has the same length and heighth as the desired ICD, the thickness of the emulator may be smaller than the ICD as long as the electrical characteristics of the emulator are similar to the ICD or in other words as long as the conductive geometry is similar. In a preferred embodiment, emulator housing 28 has a resistance of less than 1 ohm and is made of titanium, but also could be made of stainless steel (316L), biocompatible conductive polymer, or other short term biocompatible materials that appropriately simulate the electrical characteristics of the ICD, such as copper or brass. Additionally, the surface of emulator 28 may be coated with platinum or other noble metals such as nickel, iridium, gold, palladium or mercury to permit use without electrical degradation. Conductive lead 30 is comprised of a multi-stranded wire with a sterilized insulation sheath. In the preferred embodiment, conductor 30 is made of silver or copper wires with Teflon® or other common insulation. Because the emulator of the present invention is disposable, platinum iridium conductors or MP35N conductors having polyurethane or silicon insulation is not needed.

Figure 4:
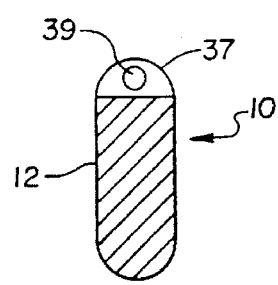
FIG. 4 is a sectional view taken along line 4—4 of FIG. 3.

FIG. 4 illustrates a cross sectional view of emulator housing 28 taken along line 4—4 of FIG. 3. As stated above, emulator housing 28 is chosen to replicate the approximate length and width of the desired implantable ICD. This is because for testing purposes, the emulator is placed in the pectoral region of a patient in the same place the desired ICD will be placed if the patient passes the screening process. By having emulator housing 28 substantially the same size as the desired ICD, a pocket can be formed in the patient by the emulator. As illustrated in FIG. 4, housing 28 has an upper flange 37 that simulates the dimensional characteristics of a header found on standard ICD leads. An intermediary tube 39 protrudes from flange 37 for connection to conductive lead 30 as will be described in detail below. Intermediary tube 39 is permanently affixed to the flange 37 by soldering or welding or other known fixation means.

Figure 5:
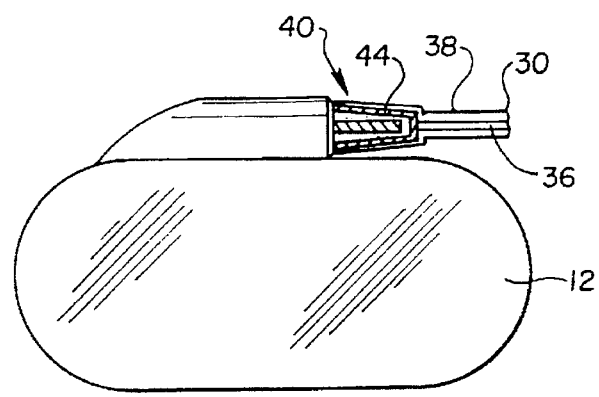
FIG. 5 is a partial sectional view of the emulator housing and lead connection according to the present invention.

FIG. 5 illustrates the connection between conductive lead 30 and emulator housing 28. As previously stated, emulator housing 28 contains upper flange 37 for simulating the header found on typical ICD's. Conductive lead 30 is comprised of multistranded wire 36 and a sterilizable insulation sheath 38 and contains a proximal connector 40 and a distal connector 42 (shown in FIG. 3). Proximal connector 40 contains an electrically conductive socket 44 electrically connected to multistranded wire 36 inside of lead 30 and encapsulated by insulation sheath 38. Socket 44 is sized slightly larger than intermediary tube 39 to receive tube 39. Proximal connector 40 is mounted onto intermediary tube 39 and is fixated to the tube by known fixation means such as welding, soldering or crimping. Alternatively, a locking fixation mechanism such as a one-way thread could be used to permanently secure connector 40 to tube 39 for the duration of the intraoperative DFT testing procedure.

Figure 6:
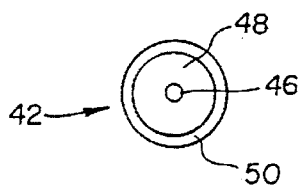
FIG. 6 is an end view of a test system connector according to the present invention.
Figure 7:
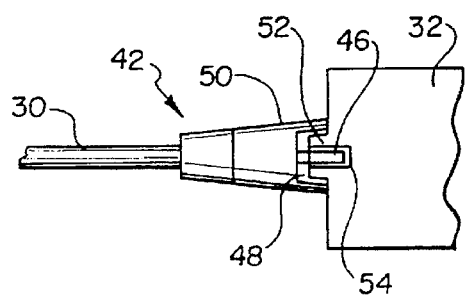
FIG. 7 is a partial sectional view of the test system connector and the test system according to the present invention.

FIG. 6 is an end view of the distal connector 42. Distal connector 42 is comprised of connector pin 46, a recessed area 48 and an operator protective shield 50. As illustrated in FIG. 2, the distal connector 42 is inserted into second connection port 35 of remote test system 32 for conducting the emulation. FIG. 7 is a cross-sectional view of a portion of the test system 32 having a distal connector 42 inserted therein. Test system 32 has a connector lip 52 surrounding a receiving hole 54. As illustrated, insertion pin 46 is inserted into receiving hole 54 which is sized to receive pin 46 while making electrical contact with the pin. Connector lip 52 fits into recess area 48 while operator protective cover 50 protects the operator from the high voltages passing through lead 30.

In a typical testing procedure for a subcutaneous implant, the skin of a patient's pectoral region is slit approximately 6 cm in length, and the emulator is inserted subcutaneously. The depth of this subcutaneous implant is approximately 5 mm. In some instances it may be desired to implant the emulator below a layer of muscle. If this is the case, a portion of the pectoral muscle is also cut and the emulator is implanted beneath a layer of the muscle. In this case, the emulator is approximately 2 cm below the surface of the skin.

Figure 8:
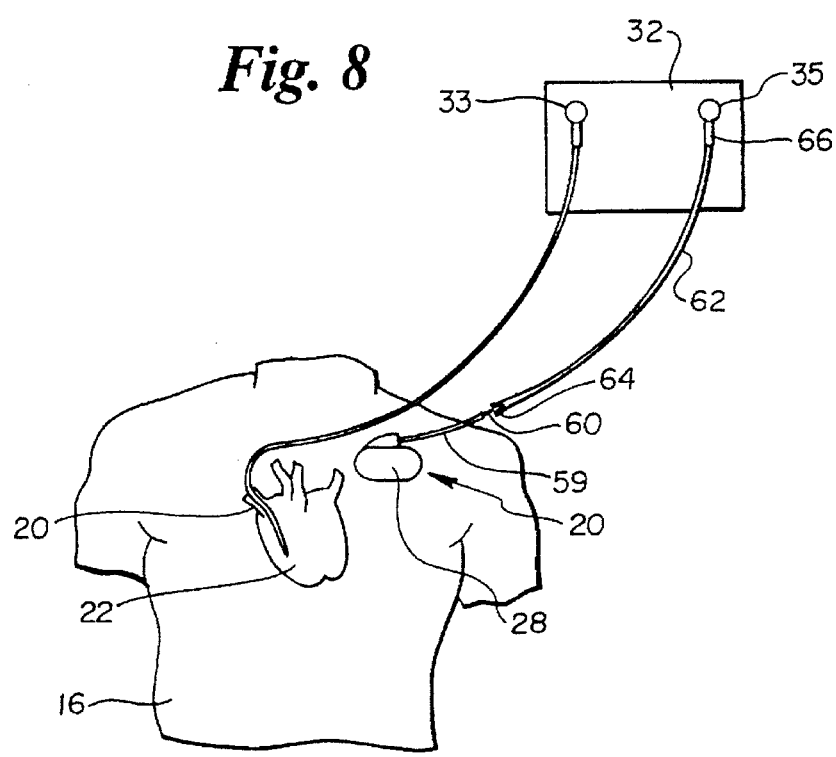
FIG. 8 is a frontal plan view of an alternative embodiment of the present invention illustrating a one piece disposable pulse generator emulator implanted in the pectoral region of a human patient connected to an external test system.
Figure 9:
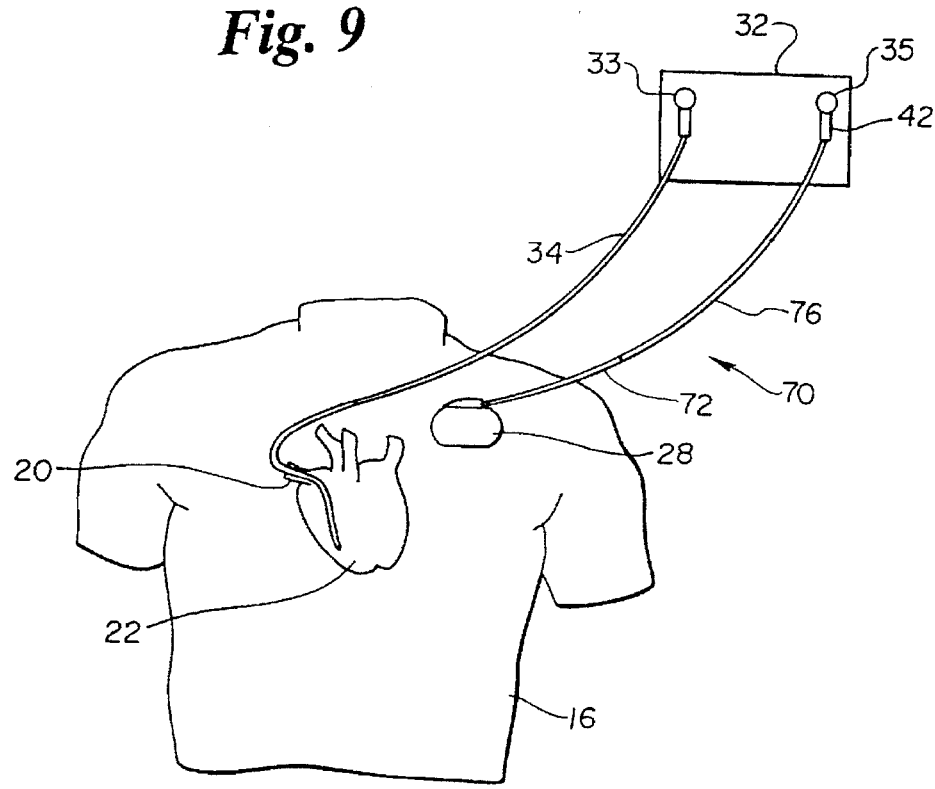
FIG. 9 is a frontal plan view of a second alternative embodiment of the present invention illustrating a one piece disposable pulse generator emulator implanted in the pectoral region of a human patient connected to an external test system.

FIGS. 8 and 9 illustrate alternative embodiments of the present invention, in which corresponding elements will have like reference numerals. Because the emulator housing 28 is only implanted into the body approximately 2 cm at the most, only a very small amount of conductive lead 30 is in contact with bodily fluids. In a first alternative embodiment of the present invention, as illustrated in FIG. 8, conductive lead 30 is replaced with lead 59 which is only long enough to protrude from the pectoral region of patient 16. Conductive lead 59 extends approximately 5 cm from patient 16 and ends in a connector 60.

A jumper cable 62 is provided having first and second connector ends 64, 66 respectively. First connector end 64 is releasably connectable to connector 60 and second connector end 66 is releasably connectable to test unit 32. Connectors 64, 66 may be any type of known connectors capable of handling large voltages. Jumper cable 62 need not be made of biocompatible material because it is not in contact with the body, therefore it may be made of inexpensive, non-biocompatible materials. Only conductive lead 59 must be made of biocompatible material, and like conductive lead 30, because it will be disposed of after DFT testing of each patient it need not be platinum iridium or MP35N having polyurethane or silicon insulation as in standard ICD leads, but may be made of silver or copper wires with Teflon® or other common insulation. When testing is completed, emulator 26 and conductive lead 59 are disposed of, but jumper cable 62 is not.

FIG. 9 illustrates a second alternative embodiment of the present invention. A conductive lead 70 is provided extending from emulator housing 12 to test system 32. Conductive lead 70 is divided into a biocompatible portion 72 and a non-biocompatible portion 74 at dividing point 76. Lead portion 72 is approximately 5 cm long and is the portion of lead 70 directly adjacent to emulator housing 28. Lead portion 72 is biocompatible because it is in contact with bodily fluids. Lead portion 74 connects to test system 32 and is not biocompatible because it is not in direct contact with the body. As with the previous alternative embodiment, this allows the larger portion of lead 70, portion 74, to be constructed of less expensive non biocompatible materials.

We claim:

1. A one piece, disposable pulse generator emulator for emulating a subcutaneous pulse generator having a housing that forms an active housing electrode for use with a remote test system to screen a patient for candidacy for implantation of a desired pulse generator, the emulator comprising:

an emulator housing having substantially the same conductive geometry as the desired implantable pulse generator;

a lead having proximal and distal ends, the proximal end being permanently, fixedly attached to the emulator housing; and a test system connector permanently, fixedly attached to the distal end of the lead for connection to the remote test system:

such that the housing, the lead and the connector form a unitary device in which the housing and the lead are permanently secured to each other.

2. The emulator of claim 1 wherein the emulator housing has a length and a width substantially the same as that of the desired implantable pulse generator.

3. The emulator of claim 1 wherein the emulator housing is thinner than the desired implantable pulse generator.

4. The emulator of claim 1 wherein the emulator housing has a resistance of less than one ohm.

5. The emulator of claim 1 wherein the lead comprises a plurality of conductors having a sterilizable insulation sheath thereabout.

6. The emulator of claim 1 wherein the emulator housing has an upper flange, integral with the emulator housing and wherein the proximal end of the lead is connected to the emulator housing at the upper flange.

7. The emulator of claim 6 wherein the upper flange is substantially similar in size to a header on the desired pulse generator.

8. The emulator of claim 1 further comprising a jumper cable for electrically connecting the test system connector to the remote test system.

9. The emulator of claim 8 wherein the lead has a length of approximately 5 cm.

10. The emulator of claim 1 wherein the lead has a biocompatible insulation sheath for approximately 5 cm adjacent the proximal end and a non-biocompatible insulation sheath about the remainder of the lead.

11. An active housing emulation system comprising:

an integral, disposable emulator housing and a lead unit wherein the housing forms an active electrode and has substantially the same conductive geometry as a desired implantable pulse generator, and wherein the lead unit has proximal and distal ends wherein the proximal end is permanently, fixedly attached to the housing such that the housing and the lead unit are permanently secured to each other;

an implantable electrode lead implantable in a desired permanent location of a patient's body; and an external test system electrically connected to the distal end of the emulator housing lead unit and to the implantable electrode lead.

12. The emulator of claim 11 wherein the emulator housing has a length and a width substantially the same as that of the desired implantable pulse generator.

13. The emulator of claim 11 wherein the emulator housing is thinner than the desired implantable pulse generator.

14. The emulator of claim 11 wherein the emulator housing has a resistance of less than one ohm.

15. The emulator of claim 11 wherein the lead unit comprises a plurality of conductors having a sterilizable insulation sheath thereabout.

16. The emulator of claim 11 wherein the emulator housing has an upper flange, integral therewith and wherein the proximal end of the lead unit is connected to the emulator housing at the upper flange.

17. The emulator of claim 16 wherein the upper flange is substantially similar in size to a header on the desired pulse generator.

18. The emulator of claim 11 further comprising a jumper cable for electrically connecting the lead unit to the external test system.

19. The emulator of claim 18 wherein the lead has a length of approximately 5 cm.

20. The emulator of claim 11 wherein the lead has a biocompatible insulation sheath for approximately 5 cm adjacent the proximal end and a non-biocompatible insulation sheath about the remainder of the lead.

21. A method of screening a patient for candidacy for implantation of a desired pulse generator having an active housing electrode, the method including the steps of:

(a) implanting a first conductive lead into the patient's body wherein the first conductive lead is intended to remain in place if the patient is fitted with the desired pulse generator;

(b) implanting a one piece, disposable pulse generator emulator into the pectoral region of the patient wherein the disposable pulse generator emulator has a second conductive lead fixedly attached thereto;

(c) providing an external test system which simulates operation of the desired pulse generator;

(d) electrically connecting the first conductive lead and the second conductive lead to the external test system;

(e) conducting the patient screening;

(f) disconnecting the first and second conductive leads from the external test system; and (g) disposing of the one piece, disposable pulse generator emulator when the testing is complete.

* * * * *

UNITED STATES PATENT AND TRADEMARK OFFICE
CERTIFICATE OF CORRECTION

PATENT NO. : 5,662,696
DATED : Sep. 2, 1997
INVENTOR(S) : Mark Kroll, Roger Dahl, Stephen Sundquist, Nelson It is certified that error appears in the above-identified patent and that said Letters Patent is hereby corrected as shown below:

On the title page, insert --[73] Angeion Corporation, Brooklyn Park, Minnesota--.

Signed and Sealed this

Thirteenth Day of April, 1999

Attest:

Q. TODD DICKINSON

Attesting Officer

Acting Commissioner of Patents and Trademarks